(12) United States Patent
Nightingale et al.

(10) Patent No.: US 7,602,963 B2
(45) Date of Patent: Oct. 13, 2009

(54) METHOD AND APPARATUS FOR FINDING ANOMALIES IN FINISHED PARTS AND/OR ASSEMBLIES

(75) Inventors: Gerald B. Nightingale, West Chester, OH (US); Francis Howard Little, Cincinnati, OH (US); John C. Janning, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 652 days.

(21) Appl. No.: 11/328,878

(22) Filed: Jan. 10, 2006

(65) Prior Publication Data

US 2007/0160282 A1    Jul. 12, 2007

(51) Int. Cl.
*G06K 9/00* (2006.01)
(52) U.S. Cl. .................. 382/149; 382/152; 382/154
(58) Field of Classification Search ............. 382/141, 382/149, 152, 154
See application file for complete search history.

(56) References Cited

U.S. PATENT DOCUMENTS

| | | | |
|---|---|---|---|
| 5,111,048 A | 5/1992 | Devitt et al. | |
| 5,345,514 A | 9/1994 | Mahdavieh et al. | |
| 5,848,115 A * | 12/1998 | Little et al. | 378/4 |
| 6,041,132 A | 3/2000 | Isaacs et al. | |
| 6,285,449 B1 | 9/2001 | Ellingson et al. | |
| 6,683,641 B1 | 1/2004 | MacCracken et al. | |
| 6,968,730 B2 | 11/2005 | Schafrik et al. | |
| 7,095,221 B2 | 8/2006 | Bosselmann et al. | |
| 7,149,339 B2 | 12/2006 | Veneruso | |
| 2003/0135846 A1* | 7/2003 | Jayaram et al. | 717/137 |
| 2004/0254758 A1* | 12/2004 | Chang | 702/155 |

FOREIGN PATENT DOCUMENTS

EP        0875751 A1    4/1998

OTHER PUBLICATIONS

Obrist, Flisch, Hofmann, "Point Cloud Reconstruction with Sub-Pixel Accuracy by Slice-Adaptive Thresholding of X-Ray Computed Tomography images," NDT & E International, Butterworth-Heinemann, Oxford, GB, vol. 37(5):375-380 (Jul. 5, 2004).*
Partial European Search Report, App. No. EP 07 10 0324, (Apr. 24, 2007).
Sulzmann, et al., "Augmented Reality as an Interactive Tool for Microscopic Imaging, Measurement and Model Based Verification of Simulated Parts," Retrieved from the Internet: URL: http://www.nsti.org/publ/MSM98/W1402.pdf>, pp. 194-198 (1998).

(Continued)

*Primary Examiner*—Jon Chang
(74) *Attorney, Agent, or Firm*—William Scott Andes, Esq.; Armstrong Teasdale LLP

(57) ABSTRACT

A method for non-destructive examination of parts includes producing a 3-D image of a sample of a part, extracting a point cloud of the image of the sample of the part, and registering the point cloud to a CAD coordinate system. The method further includes determining points in the point cloud of the image that are more than a specified distance from surfaces on a CAD 3-D model of the part using the same coordinate system, and utilizing the determined points to determine the presence of anomalies or present an image of anomalies in the sample of the part.

17 Claims, 16 Drawing Sheets

OTHER PUBLICATIONS

Christian Schutz, Geometric point matching of free-form 3D objects, Retrieved from the Internet: URL: http://www-imt.unine.ch/parlab/pub/the sis/csthesis/theseSchutz.pdf>, pp. 1-147 (1998).

Prieto, et al., "An Automated Inspection System," Abstract Only. The Int'l J of Advanced Mfg Tech 19:12 (Jun. 2002) Retrieved on-line (http://www.springerlink.com/content) on May 17, 2007.

Gomercic, et al., "Robot-based 3D imaging in industrial inspection." Abstract Only. Industrial Informatics, 2004. Retrieved on-line (http://ieeexplore.ieee.org/xpl/absprintf.jsp) on May 17, 2007.

Hofmann, et al., "Adaptive CT scanning—mesh based optimisation methods for industrial x-ray computed tomography applications." Abstract Only. NDT&E International 37(2004):271-278. Retrieved on-line (http://www.empa.ch/plugin/bean/empa) on May 17, 2007.

Yancey, et al., "CT-assisted metrology for manufacturing applications." Abstract Only. Proceedings of SPIE—vol. 2948 pp. 222-231 (Nov. 1996). Retrieved on-line (http://spiedigitallibrary.aip.org/vsearch/servlet) on May 17, 2007.

Bauer, et al., "Computer tomography for nondestructive testing in the automotive industry," Abstract Only. Proceedings of SPIE—vol. 5535, pp. 464-472 (Oct. 2004). Retrieved on-line (http://spiedigitallibrary.aip.org/vsearch) on May 17, 2007.

European Search Report, App. No. EP 07 10 0324, (Jul. 25, 2007).

Sulzmann, et al., "Augmented Reality as an Interactive Tool for Microscopic Imaging, Measurement and Model Based Verification of Simulated Parts," Retrieved from the Internet: URL: http://www.nsti.org/publ/MSM98/W1402.pdf>, pp. 194-198 (1998) (Previously submitted on Jun. 11, 2007).

Christian Schutz, Geometric point matching of free-form 3D objects, Retrieved from the Internet: URL: http://www-imt.unine.ch/parlab/pub/the sis/csthesis/theseSchutz.pdf>, pp. 1-147 (1998)(Previously submitted on Jun. 11, 2007).

Prieto, et al., "An Automated Inspection System," Abstract Only. The Int'l J of Advanced Mfg Tech 19:12 (Jun. 2002) Retrieved on-line (http://www.springerlink.com/content) on May 17, 2007.(Previously submitted on Jun. 11, 2007).

Gomercic, et al., "Robot-based 3D imaging in industrial inspection." Abstract Only. Industrial Informatics, 2004. Retrieved on-line (http://ieeexplore.ieee.org/xpl/absprintf.jsp) on May 17, 2007 (Previously submitted on Jun. 11, 2007).

Yancey, et al., "CT-assisted metrology for manufacturing applications." Abstract Only. Proceedings of SPIE—vol. 2948 pp. 222-231 (Nov. 1996). Retrieved on-line (http://spiedigitallibrary.aip.org/vsearch/servlet) on May 17, 2007 (Previously submitted on Jun. 11, 2007).

Bauer, et al., "Computer tomography for nondestructive testing in the automotive industry," Abstract Only. Proceedings of SPIE—vol. 5535, pp. 464-472 (Oct. 2004). Retrieved on-line (http://spiedigitallibrary.aip.org/vsearch) on May 17, 2007. (Previously submitted on Jun. 11, 2007).

Stanley, et al., "Reverse Engineering and Rapid Prototyping for Solid Freeform Fabrication," SPIE, vol. 2455, pp. 306-311 (1995).

Lee, et al., "Development of Metrological NDE Methods for Microturbine Ceramic Components," 45th ASME Gas Turbine and Aeroengine Symposium [Online]. Retrieved on-line (http://www.ornl.gov/sci/de_materials/documents/ceramic_reliability/Lee_Devel_%20 Metro_NDE_Methods-ASME-2000.pdf>) (Jul. 24, 2007).

Flisch, et al., "Industrial Computed Tomography in Reverse Engineering Applications," No. 8, pp. 45-53 XP002444033, Computerized Tomography for Industrial Applications and Image Processing in Radiology, Mar. 15-17, 1999, Berlin, Germany.

Obrist, et al., "Point Cloud Reconstruction with Sub-Pixel Accuracy by Slice-Adaptive Thresholding of X-Ray Computed Tomography Images," NDT & E International, Butterworth-Heinemann, Oxford, GB, vol. 37(5):373-380 (Jul. 5, 2004).

* cited by examiner

METHOD AND APPARATUS FOR FINDING ANOMALIES IN FINISHED PARTS AND/OR ASSEMBLIES

BACKGROUND OF THE INVENTION

This invention relates generally to inspection of parts, and more particularly to the detection of anomalies in finished manufactured parts.

During the manufacturing of complex 3D structures, there is a possibility of foreign material occurring in internal passages or cavities. For example, in the machining of complex parts or assemblies with inner passages, machine chips may lodge inside. If the passages do not easily allow either visual or mechanical access, it may be difficult to be absolutely sure no chips remain inside.

In the manufacture of turbine blades for aircraft, a ceramic core is often used to form complex inner cooling air passages. To check whether the ceramic core has been removed by a subsequent chemical cleaning, the blades are often sent for neutron radiography, which results in the loss of considerable time in the manufacturing and approval process. Parts are often laser drilled or EDM (electron discharge machining) drilled to form cooling holes. Sometimes these holes converge, and it may be difficult to detect the exact point of convergence. In addition, pipes and parts may suffer corrosion or erosion in use, and it is not easy to determine how much good material remains.

Non-destructive examination of parts can be performed by one or more known techniques, which include, for example, radiography, ultrasonics, and acoustic emission. For the most exact location of problems inside parts it has been found that computed tomography showing cross sections is most helpful.

BRIEF DESCRIPTION OF THE INVENTION

Therefore, in one aspect, some configurations of the present invention provide a method for non-destructive examination of parts. The method includes producing a 3-D image of a sample of a part, extracting a point cloud of the image of the sample of the part, and registering the point cloud to a CAD coordinate system. The method further includes determining points in the point cloud of the image that are more than a specified distance from surfaces on a CAD 3-D model of the part using the same coordinate system, and utilizing the determined points to determine the presence of anomalies or present an image of anomalies in the sample of the part.

In another aspect, some configurations of the present invention provide an apparatus for non-destructive examination of parts. The apparatus includes a computer having a display and memory, and the computer configured to extract a point cloud from a 3-D image of a sample of a part, and register the point cloud to a CAD coordinate system. The apparatus is further configured to determine points in the point cloud of the image that are more than a specified distance from surfaces on a CAD 3-D model of the part using the same CAD coordinate system, and utilize the determined points to determine the presence of anomalies or present an image of anomalies in the sample of the part.

In yet another aspect, some configurations of the present invention provide a machine-readable medium or media having recorded thereon instructions. The recorded instructions are configured to instruct a computer to extract a point cloud from a 3-D image of a sample of a part, register the point cloud to a CAD coordinate system, determine points in the point cloud of the image that are more than a specified distance from surfaces on a CAD 3-D model of the part using the same CAD coordinate system, and utilize the determined points to determine the presence of anomalies or present an image of anomalies in the sample of the part.

Configurations of the present invention can be used to find anomalies in finished parts. It will be appreciated that configurations of the present invention can be used to produce high quality complex machined components and assemblies (i.e., parts).

DETAILED DESCRIPTION OF THE INVENTION

In some configurations of the present invention, a point cloud is extracted from a computed tomography 3D model showing all boundaries inside and outside a part, including boundaries of features that are not there by design. With a CAD model of the part there is the opportunity to use this model for subtracting that point data from the CAD model of the part in question leaving any anomaly in isolation. Manual selection of thresholds and tolerances can be performed for point cloud creation. Thus, technical effects of various configurations of the present invention include the creation of an image of an anomaly inside a finished part. Another technical effect of some configurations of the present invention is the recognition and determination of such anomalies. More particularly, a complete point set of data from an x-ray computed tomography system (for example) is obtained. The point cloud is registered to a CAD model. The point cloud is reduced by removing points within a specified distance to any CAD surface. The remaining points are anomalies. In the case of aircraft parts (at least), the anomalies may be, for example, machining chips (foreign material) in an internal cavity.

Figure 1:
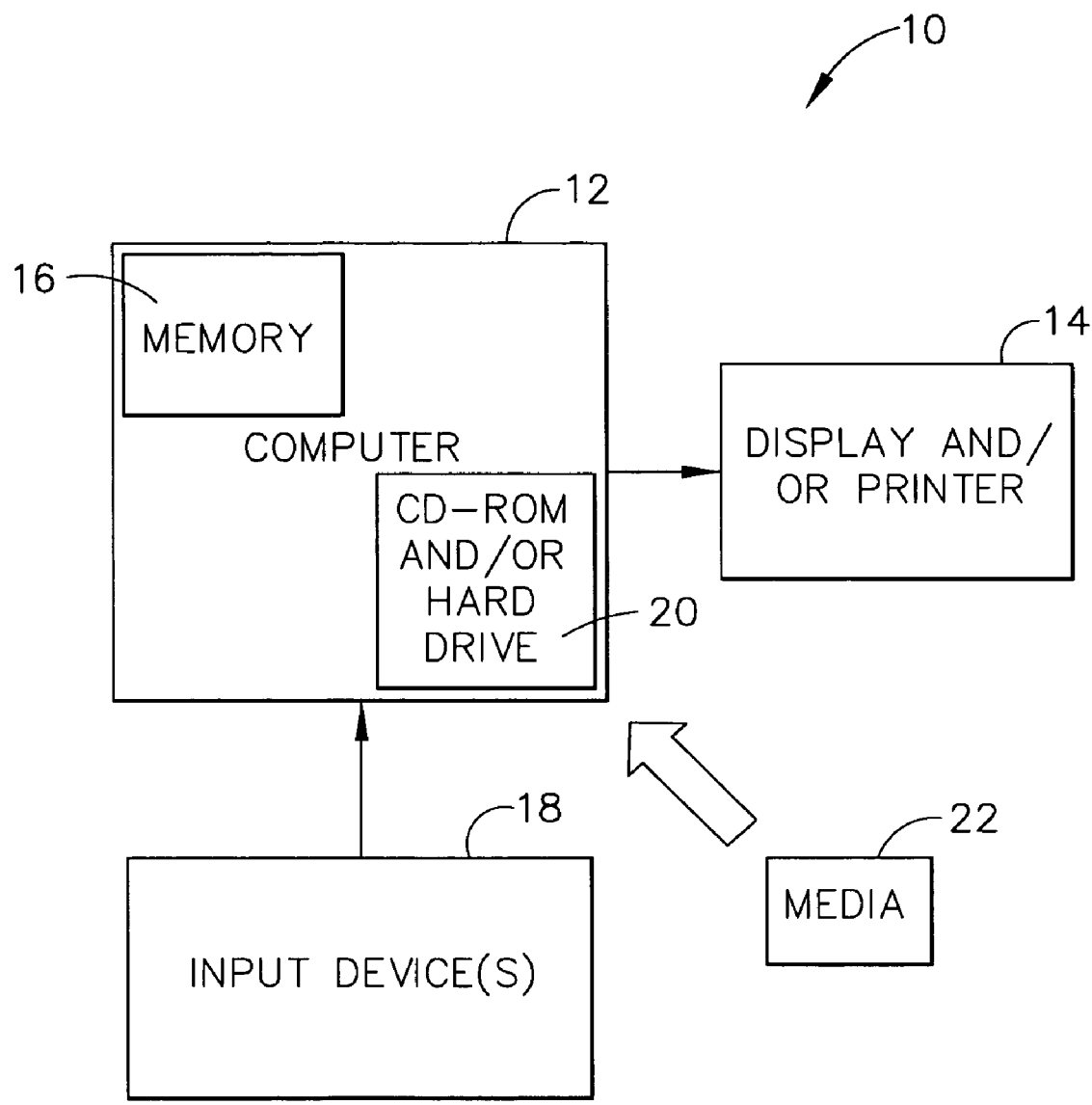
FIG. 1 is a block diagram of an apparatus configuration of the present invention.
Figure 2:
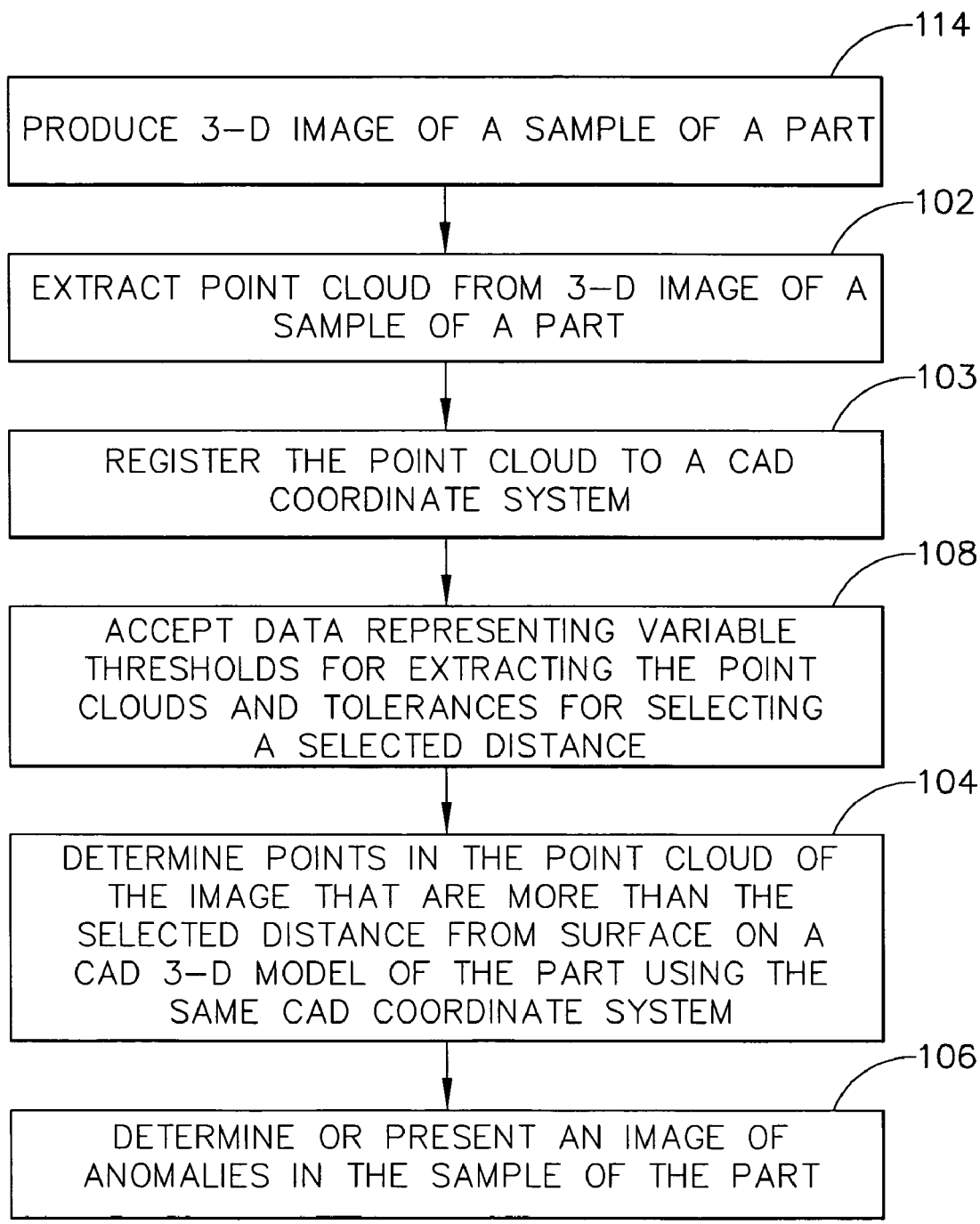
FIG. 2 is a flow chart of a method configuration of the present invention.

Thus, in some configurations and referring to FIG. 1, an apparatus 10 is provided for non-destructive examination of parts. The apparatus includes a computer 12 having a display 14 (which may be any electronic display or a printer) and memory 16. Computer 12 also may include one or more input devices 18, such as a keyboard, mouse, touch screen, light pen, etc., and one or more media devices 20 that can supply or read instructions, data, and/or data representing images, such as a hard disk, CD-ROM, floppy disk drive, CD-RW, DVD-ROM, DVD-RW, DVD+RW, flash memory, etc. In some configurations, computer 12 is connected to a network (not shown in FIG. 1) from which it may receive and/or transmit instructions, data, or data representing images. Referring to FIGS. 1 and 2, computer 12 is configured, such as via instructions recorded on medium or media 22, to extract 102 a point cloud from a 3-D image of a sample of a part, register 103 the point cloud to a CAD coordinate system, determine 104 points in the point cloud of the image that are more than a selected distance from surfaces on a CAD 3-D model of the part using the same CAD coordinate system, and utilize the determined points to determine the presence of anomalies or present 106 an image of anomalies in the sample of the part. Also in some configurations, apparatus 10 is further configured to accept 108 data representing variable thresholds (for example, via a keyboard 18) for extracting the point clouds and tolerances for selecting the selected distance. Also, in some configurations and referring to FIG. 3, to extract a point cloud, apparatus 10 is further configured to superimposing 110 a perpendicular grid on an image, and determine 112 points of the point cloud using intersections of grid lines with contrast boundaries of an image.

Figure 3:
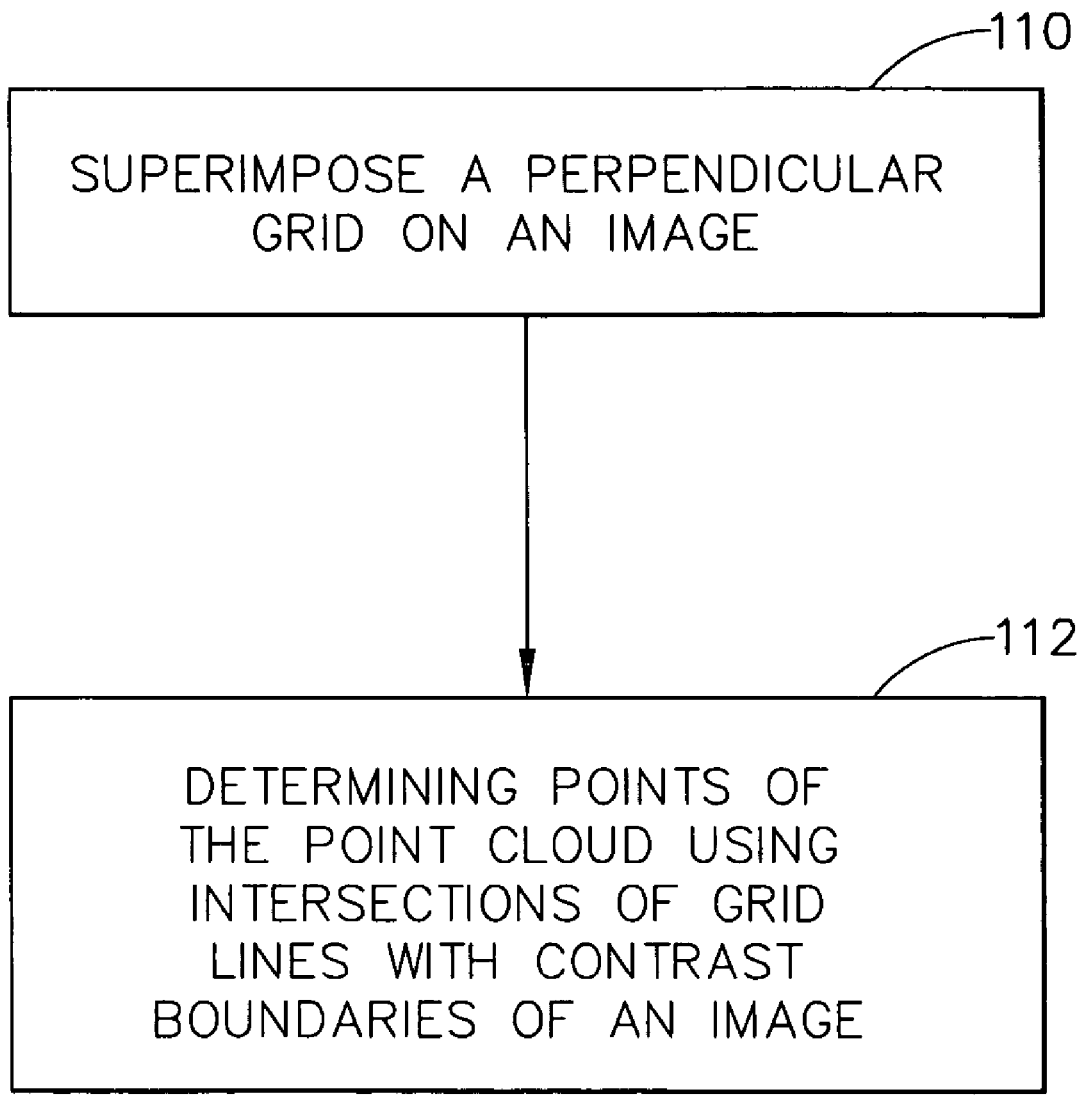
FIG. 3 is a flow chart showing a method for extracting a point cloud used in some configurations of the present invention.

In some configurations and referring to FIGS. 1, 2, and 3, a machine-readable medium or media 22 is provided having recorded thereon instructions configured to instruct a computer 12 to register 103 the point cloud to a CAD coordinate system, determine 104 points in the point cloud of the image that are more than a selected distance from surfaces on a CAD 3-D model of the part using the same CAD coordinate system, and utilize the determined points to determine the presence of anomalies or present 106 an image of anomalies in the sample of the part. In some configurations, the instructions are further configured to instruct computer 12 to accept 108 data representing variable thresholds for extracting the point clouds and tolerances for selecting the selected distance. Also, to extract a point cloud, the instructions in some configurations include instructions configured to instruct computer 12 to superimpose 110 a perpendicular grid on an image, and determine 112 points of the point cloud using intersections of grid lines with contrast boundaries of an image.

Some configurations of the present invention provide a computer-implemented method for non-destructive examination of parts. Referring to FIGS. 2 and 3, the method includes producing 114 a 3-D image of a sample of a part, extracting 102 a point cloud of the image of the sample of the part, register 103 the point cloud to a CAD coordinate system, determine 104 points in the point cloud of the image that are more than a selected distance from surfaces on a CAD 3-D model of the part using the same CAD coordinate system, and utilizing the determined points to determine the presence of anomalies or present 106 an image of anomalies in the sample of the part.

In some configurations, producing a 3-D image of a sample of the part comprises producing a computed tomographic (CT) image of the sample of the part. The CT image is, for example, a helically scanned volumetric image.

Furthermore, some configurations include setting 108 variable thresholds for extracting the point clouds and tolerances for selecting the selected distance. Also, to extract a point cloud in some configurations, the method includes superimposing 110 a perpendicular grid on an image, and determining 112 points using intersections of grid lines with contrast boundaries of an image.

Figure 4:
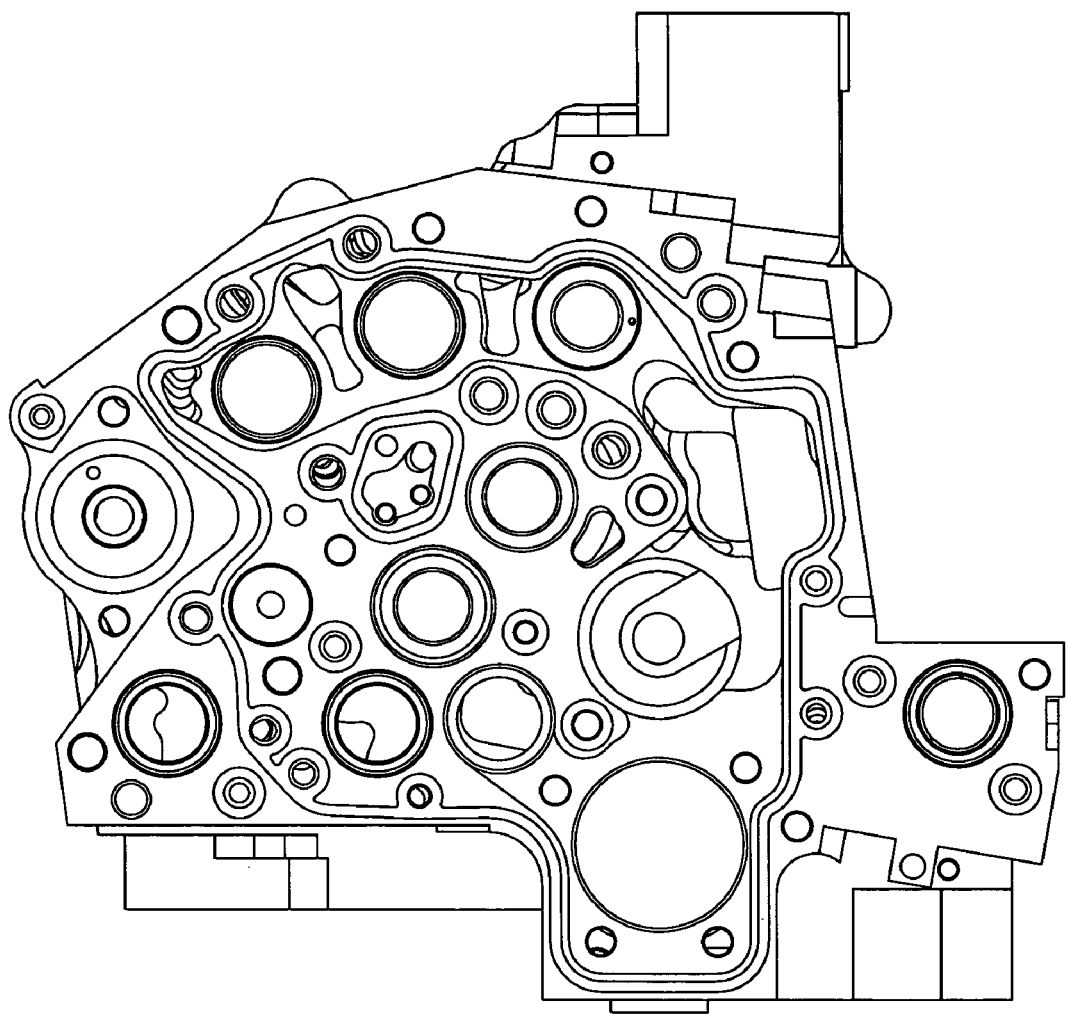
FIGS. 4, 8, and 12, are CAD drawings of a complex aircraft part at different orientations.
Figure 5:
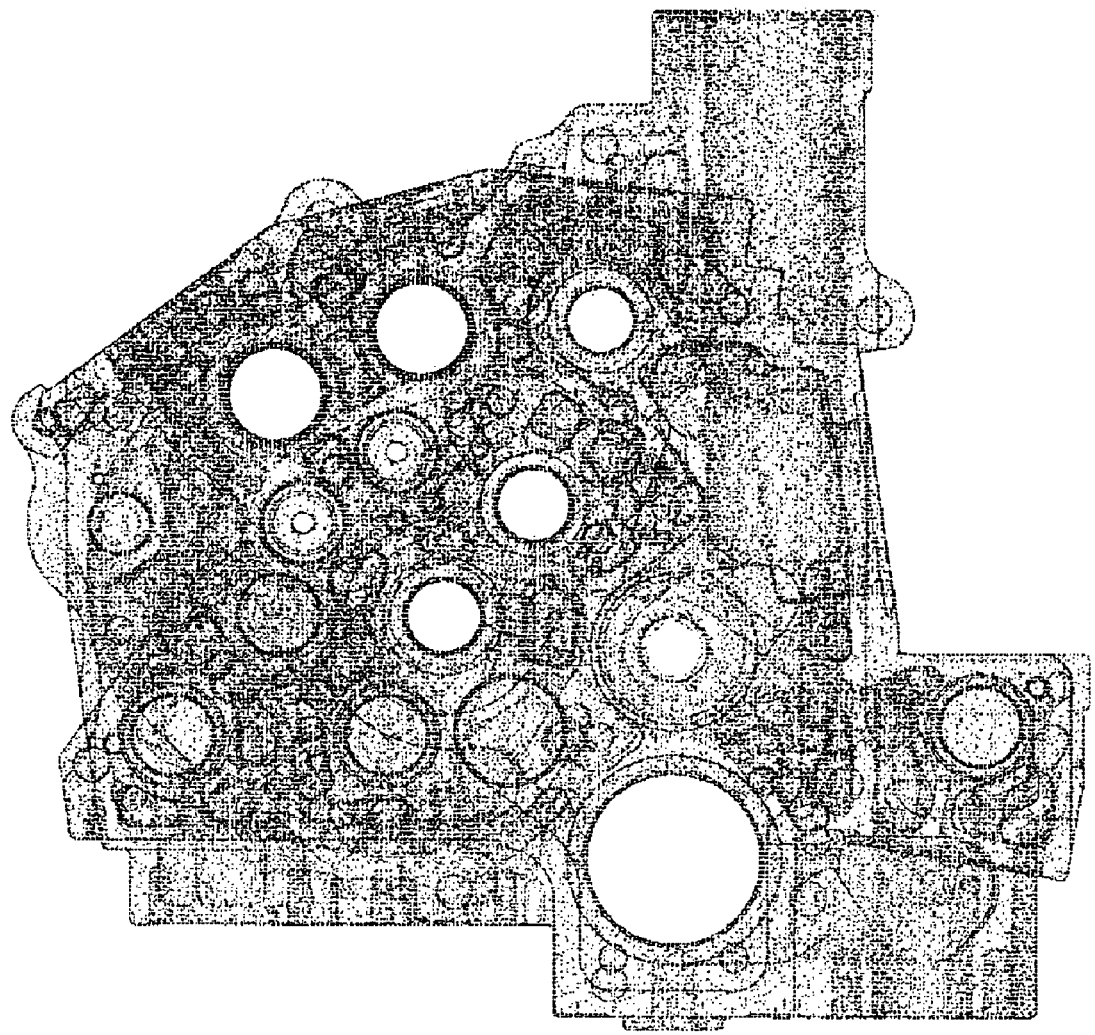
FIGS. 5, 9, and 13 are point cloud images extracted from 3-D images of a sample of the part in the CAD drawing. This sample has no flaw in it.
Figure 6:
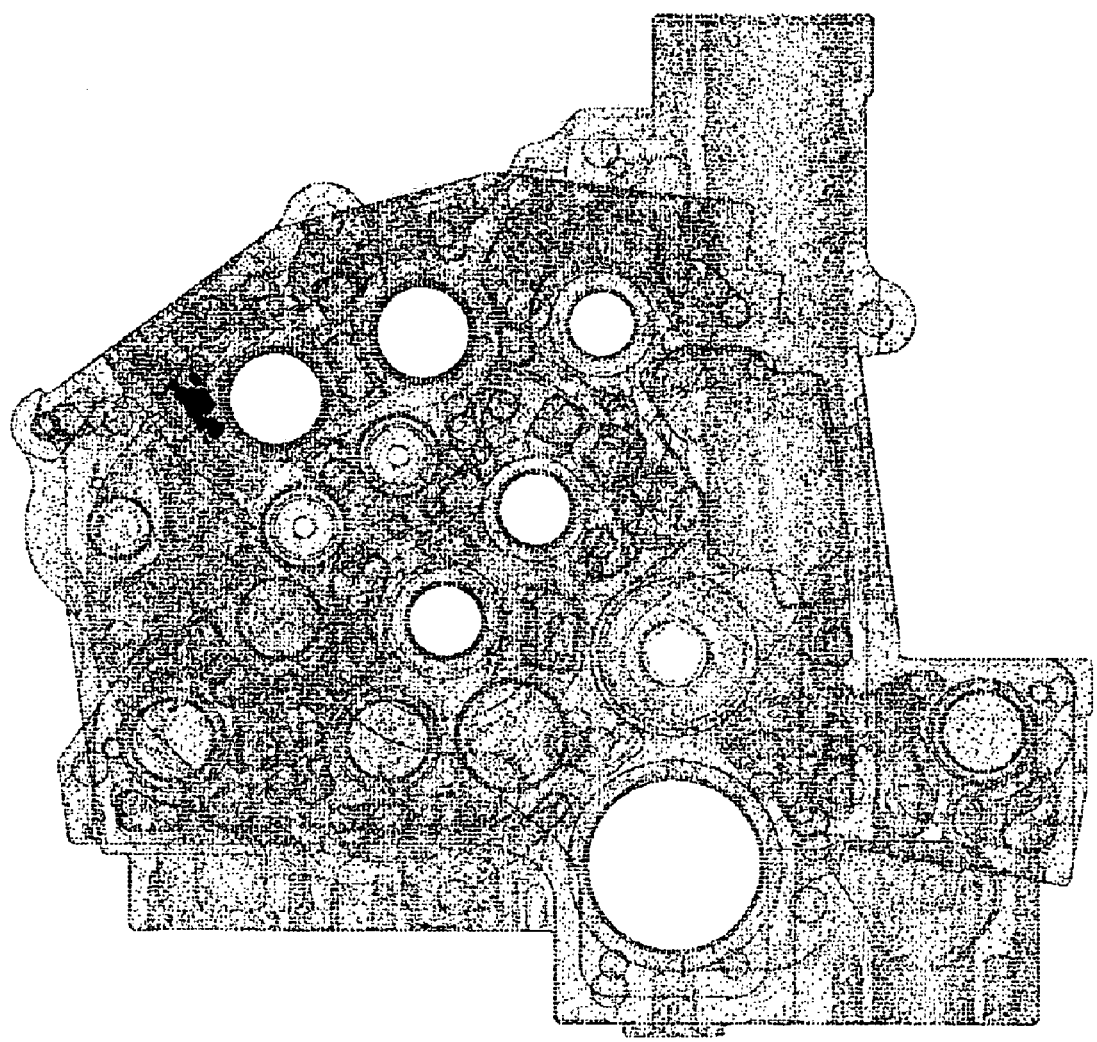
FIGS. 6, 10, and 14 are point cloud images extracted from 3-D images of another sample of that part. This sample contains a flaw.
Figure 7:
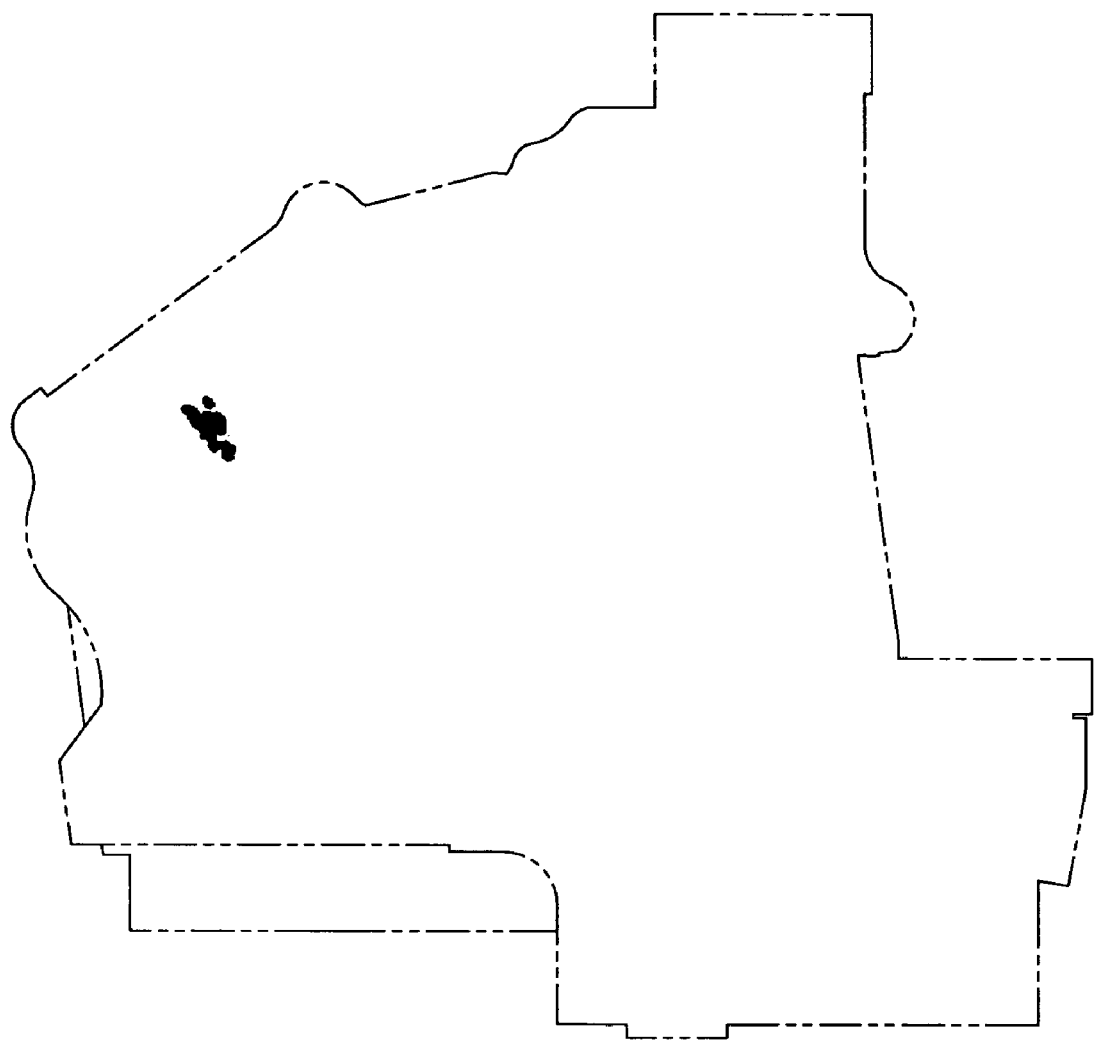
FIGS. 7, 11, and 15 are point clouds of the flaw in the sample part.
Figure 8:
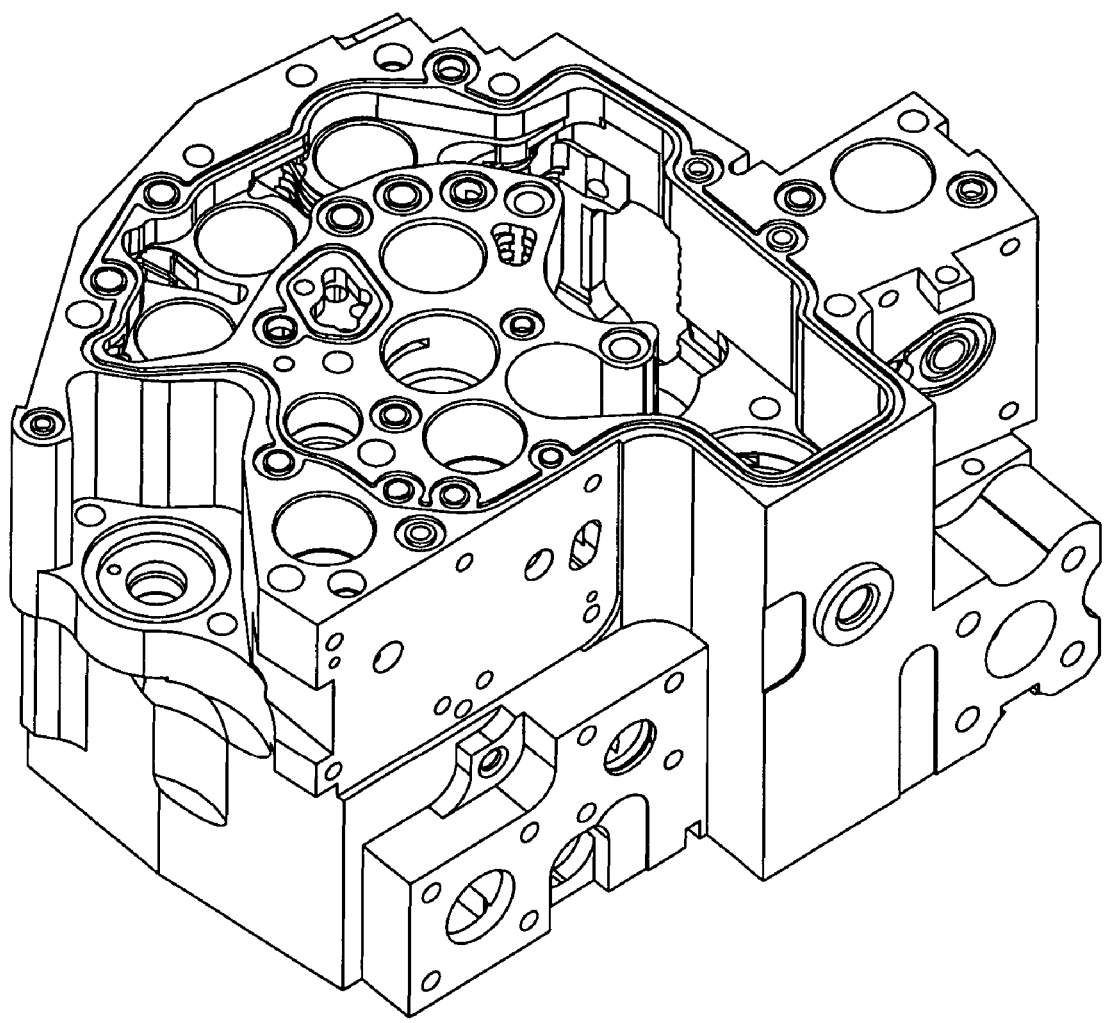
Figure 9:
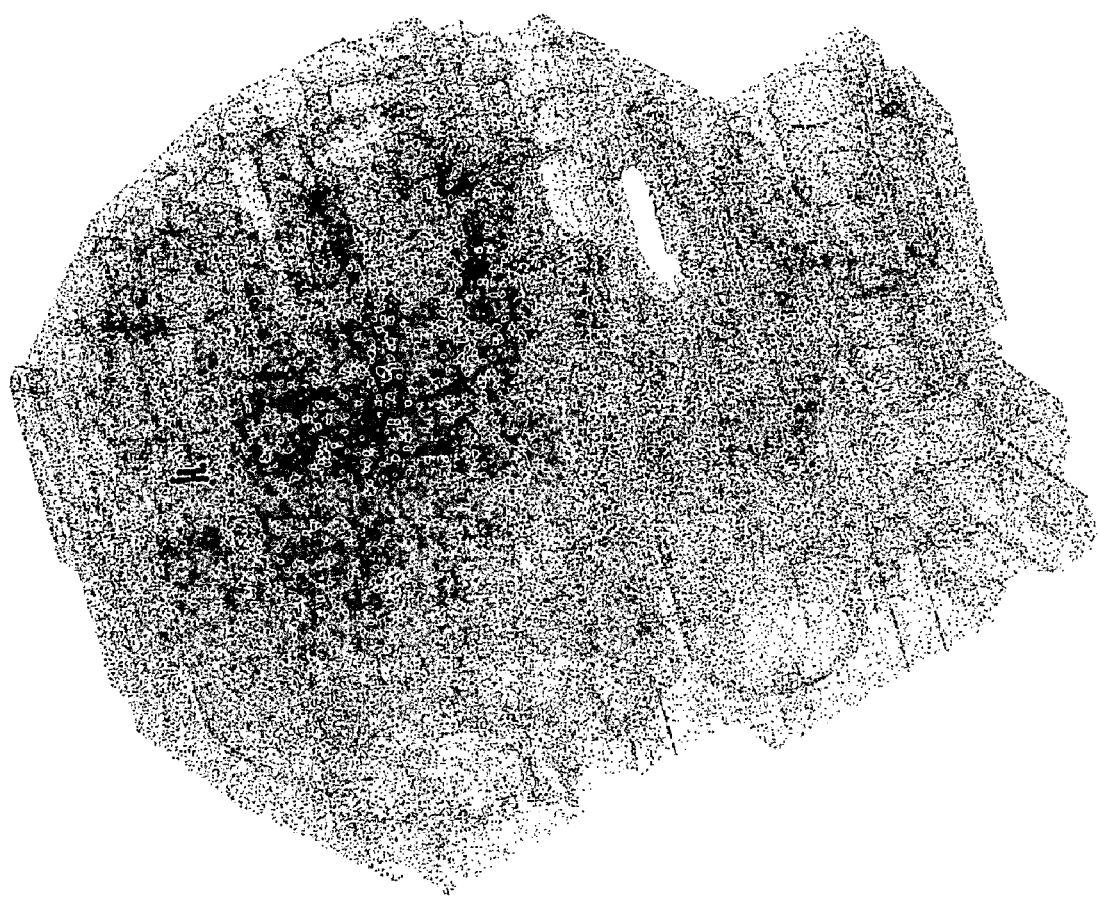
Figure 10:
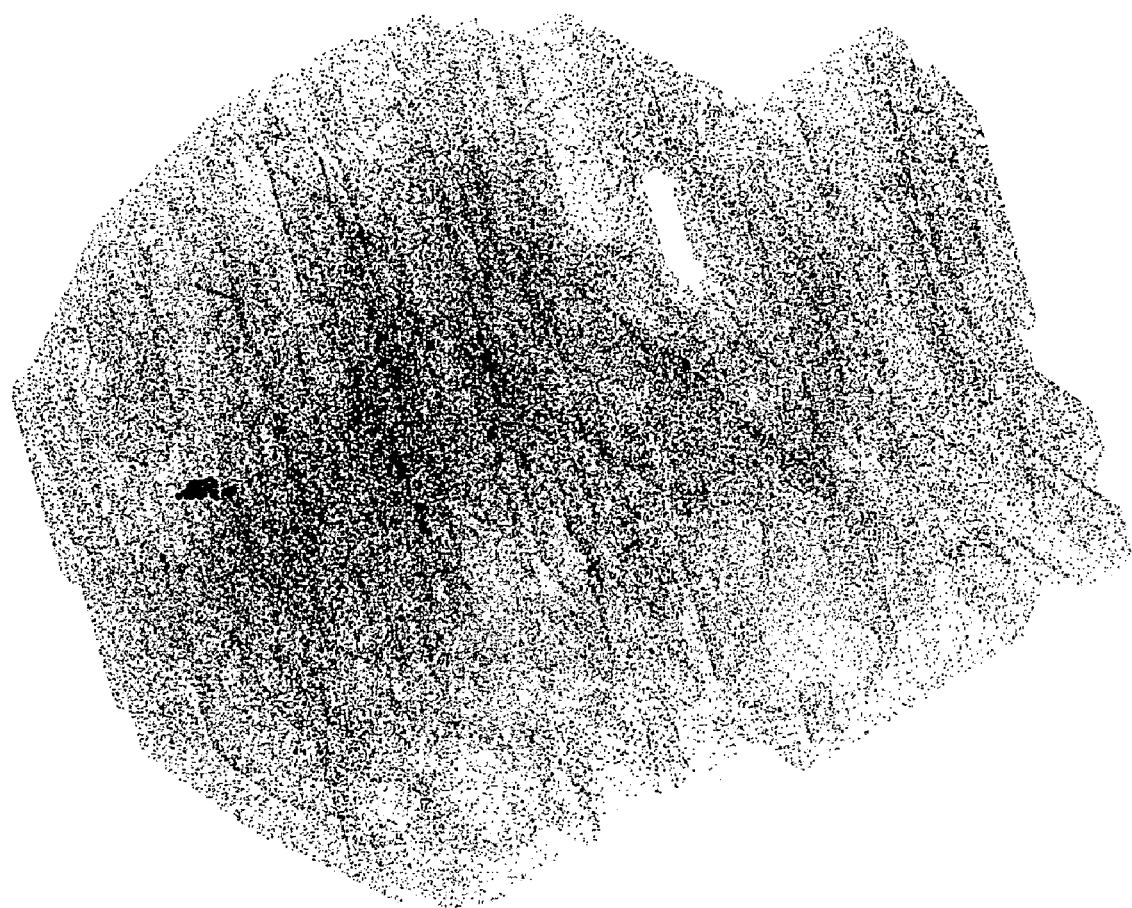
Figure 11:
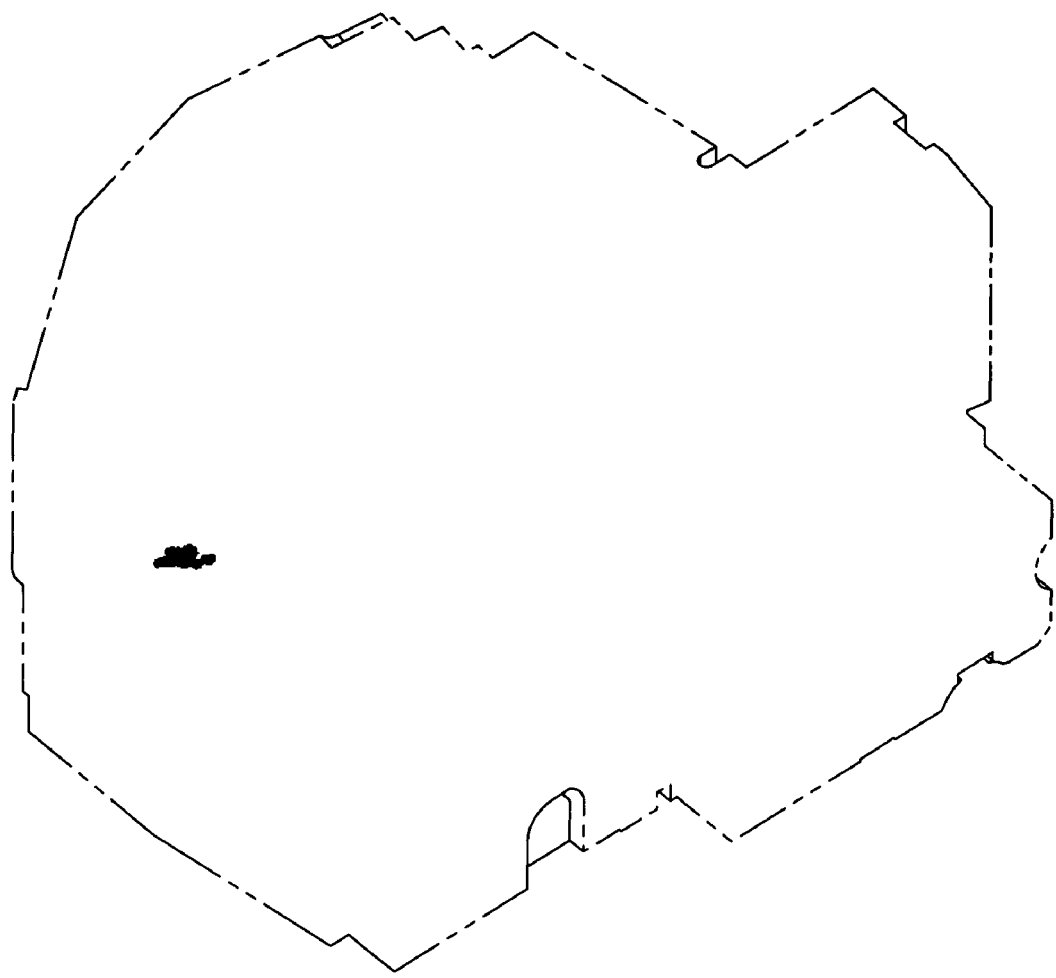
Figure 12:
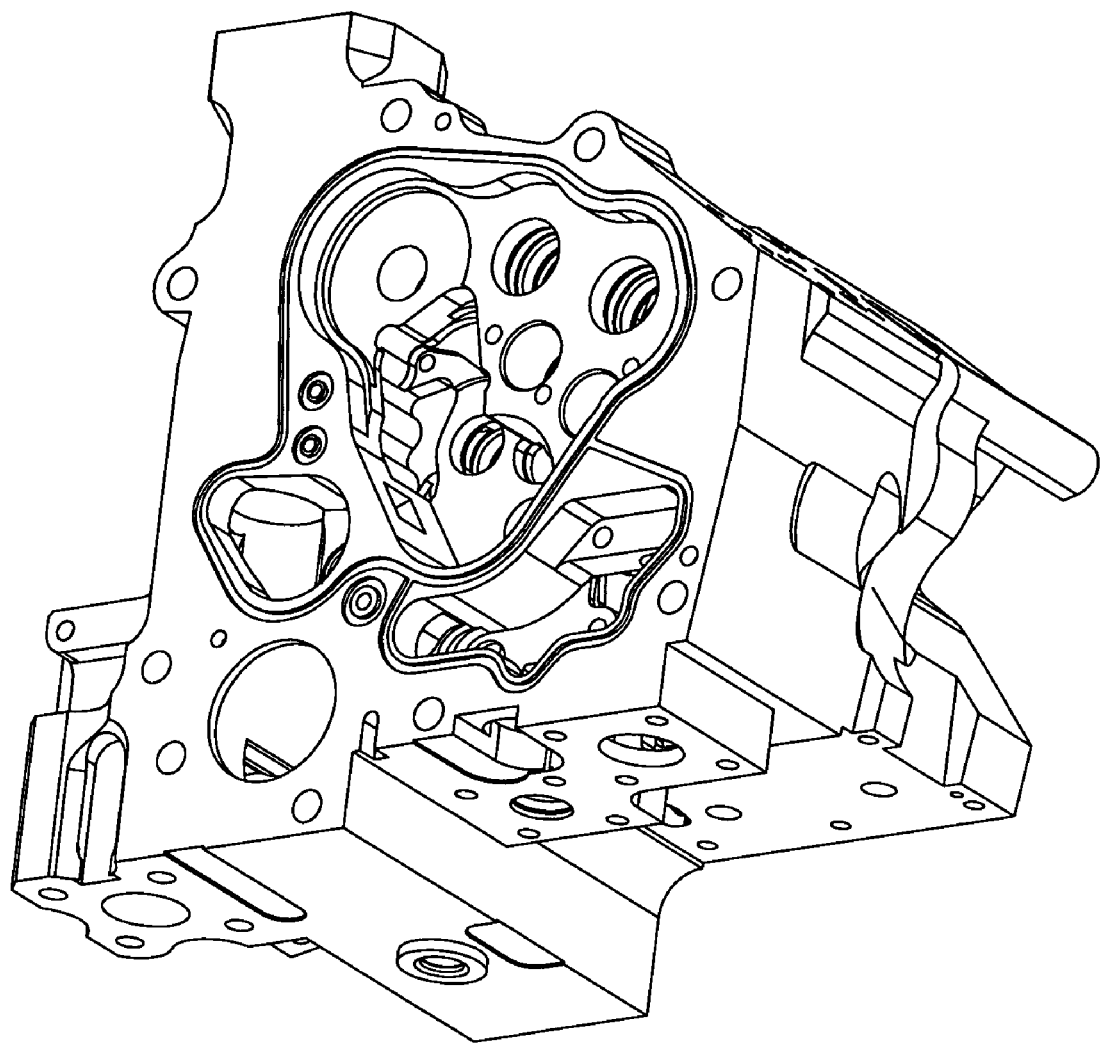
Figure 13:
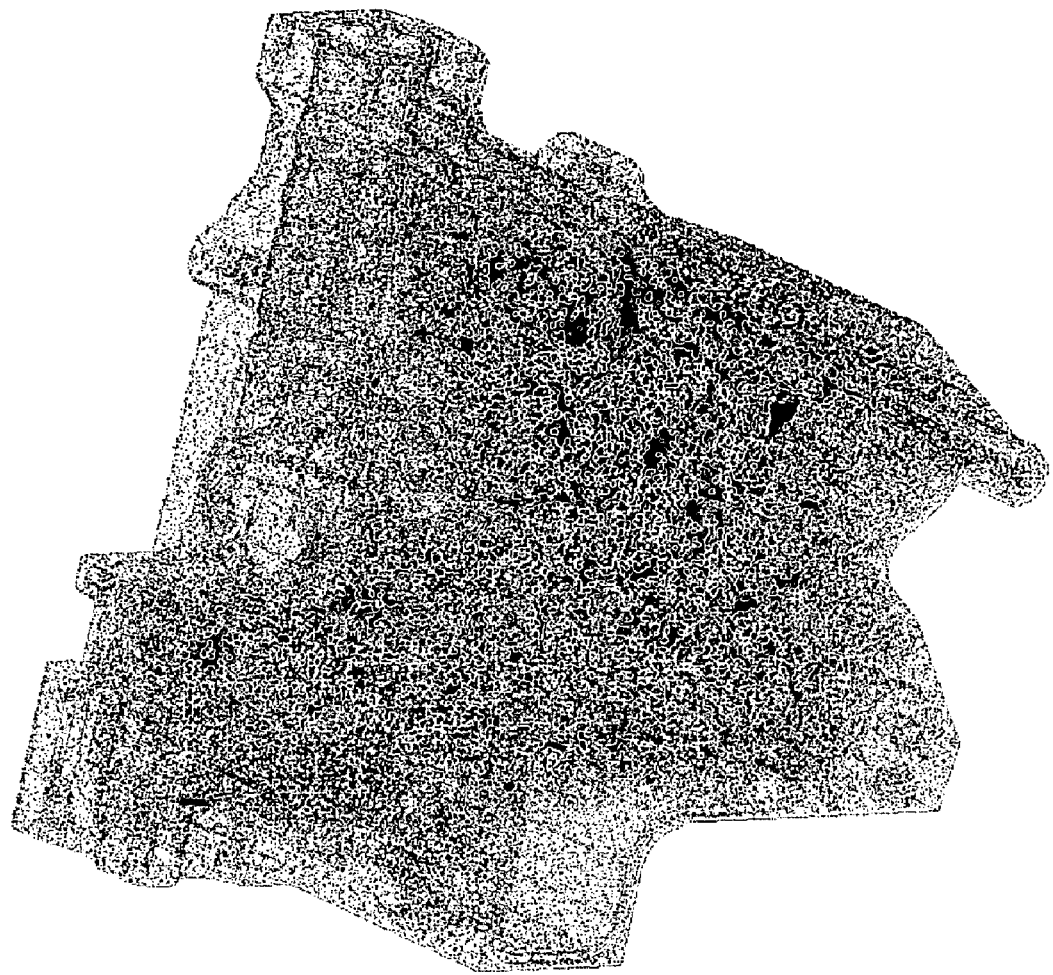
Figure 14:
Figure 15:
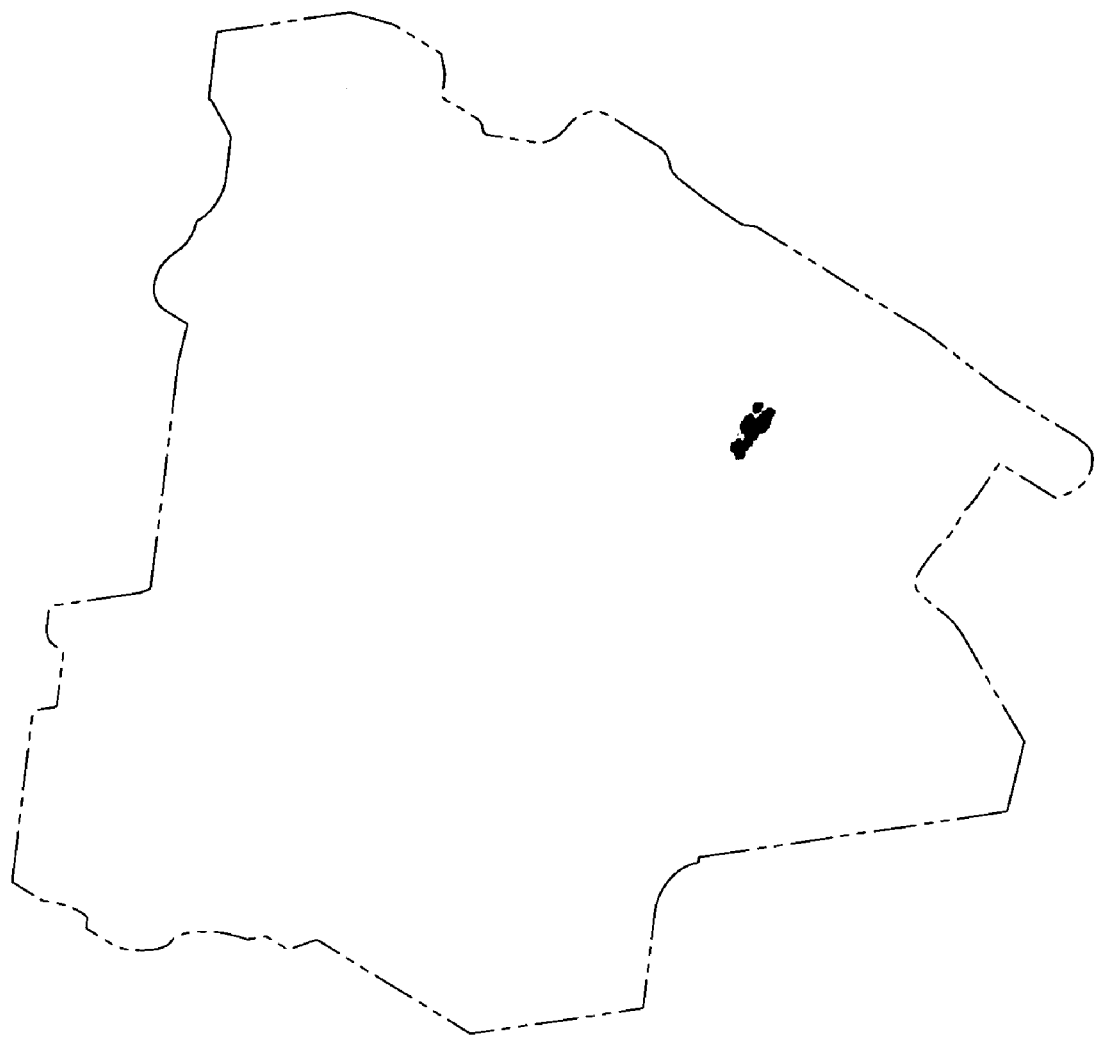

FIGS. 4, 8, and 12, are CAD drawings of a complex aircraft part at different orientations. FIGS. 5, 9, and 13 are point cloud images extracted from 3-D images of a sample of the part in the CAD drawing. This sample has no flaw in it. However, FIGS. 6, 10, and 14 are point cloud images extracted from 3-D images of another sample of that part. This sample contains a flaw. When points less than a predetermined distance from any surface in the CAD drawing are removed, the remaining points, shown in FIGS. 7, 11, and 15, illustrate the flaw in the sample part.

Figure 16:
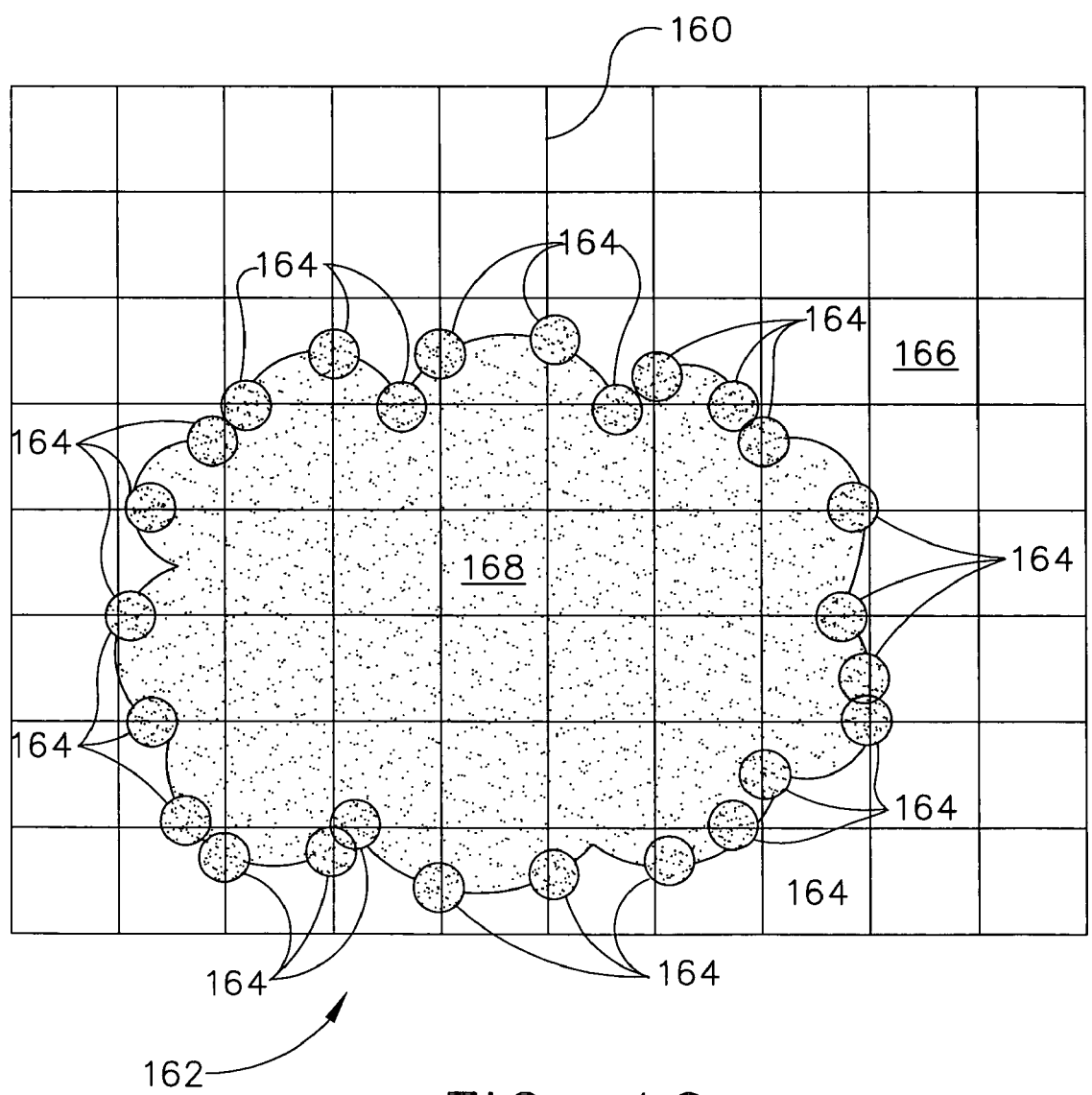
FIG. 16 illustrates a method for creating a point cloud in two dimensions.

FIG. 16 illustrates a method for creating a point cloud in two dimensions. The method can be extended in a third, perpendicular dimension to accommodate 3-D images, but is illustrated in 2-D for simplicity. A perpendicular grid 160 representing x and y directions (in 3-D, a z-direction is also used) is superimposed on an image 162 of a part, which in this example, is shown as an irregularly shaped image. The point cloud is determined as a set of points 164 that correspond to intersections of boundaries of contrasting regions 166, 168 with grid 160.

Configurations of the present invention can be used to find anomalies in finished aircraft parts, including, but not limited to turbine blades. Although methods and apparatus disclosed herein are particularly suitable for aircraft parts, their uses are not limited to aircraft part and various configurations of the present invention can be used with other types of manufactured parts. It will be appreciated that configurations of the present invention can be used to produce high quality complex machined components and assemblies (i.e., parts).

While the invention has been described in terms of various specific embodiments, those skilled in the art will recognize that the invention can be practiced with modification within the spirit and scope of the claims.

What is claimed is:

1. A method for non-destructive examination of parts, said method comprising:
   generating a 3-D image of a sample of a part using a computed tomographic imaging system;
   extracting a point cloud of the image of the sample of the part from the 3-D image;
   registering the point cloud to a CAD coordinate system;
   determining points in the point cloud of the image that are more than a selected distance from surfaces on a CAD 3-D model of the part utilizing the same CAD coordinate system;
   utilizing the determined points that are greater than the selected distance to determine the presence of anomalies; and
   outputting an image of anomalies inside or outside the sample of the part to at least one of a display and a printer.

2. A method in accordance with claim 1 wherein said generating a 3-D image of a sample of the part comprises generating a computed tomographic (CT) image of the sample of the part.

3. A method in accordance with claim 2 wherein said CT image is a helically scanned image.

4. A method in accordance with claim 3 wherein said CT image is a volumetric helically scanned image.

5. A method in accordance with claim 1 further comprising setting variable thresholds for extracting said point clouds and tolerances for selecting distance.

6. A method in accordance with claim 1 wherein to extract a point cloud, said method includes superimposing a perpendicular grid on an image, and determining points using intersections of grid lines with contrast boundaries of an image.

7. A method in accordance with claim 1 wherein said part is a finished aircraft part.

8. A method in accordance with claim 7 wherein said part is a turbine blade.

9. An apparatus for non-destructive examination of parts, said apparatus comprising:

a computer having a display and memory, and a computer-readable medium having recorded thereon instructions configured to instruct the computer to:

extract a point cloud from a 3-D image of a sample of a part;

register the point cloud to a CAD coordinate system;

determine points in the point cloud of the image that are greater than a selected distance from surfaces on a CAD 3-D model of the part utilizing the same CAD coordinate system;

utilize the determined points that are greater than the selected distance to determine the presence of anomalies; and output an image of anomalies in the sample of the part.

10. An apparatus in accordance with claim 9 further configured to accept data representing variable thresholds for extracting said point clouds and tolerances for selecting said selected distance.

11. An apparatus in accordance with claim 9 wherein to extract a point cloud, said apparatus further configured to superimpose a perpendicular grid on an image, and determine points of the point cloud using intersections of grid lines with contrast boundaries of an image.

12. A machine-readable medium or media having recorded thereon instructions configured to instruct a computer to:

extract a point cloud from a 3-D image of a sample of a part;

register the point cloud to a CAD coordinate system;

determine points in the point cloud of the image that are greater than a selected distance from surfaces on a CAD 3-D model of the part utilizing the same CAD coordinate system;

utilize the determined points that are greater than the selected distance to determine the presence of anomalies; and output an image of anomalies in the sample of the part to at least one of a display and a printer.

13. A computer-readable medium in accordance with claim 12 wherein said instructions are further configured to instruct the computer to accept data representing variable thresholds for extracting said point clouds and tolerances for selecting said selected distance.

14. A computer-readable medium in accordance with claim 12 wherein to extract a point cloud, said instructions include instructions configured to instruct the computer to superimpose a perpendicular grid on an image, and determine points of the point cloud using intersections of grid lines with contrast boundaries of an image.

15. A method in accordance with claim 1 wherein the determined points that are greater than the selected distance illustrate the anomalies inside or outside the sample of the part.

16. An apparatus in accordance with claim 9 wherein the determined points that are greater than the selected distance illustrate the anomalies in the sample of the part.

17. A computer-readable medium in accordance with claim 12 wherein the determined points that are greater than the selected distance illustrate the anomalies in the sample of the part.

* * * * *

UNITED STATES PATENT AND TRADEMARK OFFICE
CERTIFICATE OF CORRECTION

PATENT NO.      : 7,602,963 B2                        Page 1 of 1
APPLICATION NO. : 11/328878
DATED           : October 13, 2009
INVENTOR(S)     : Nightingale et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this

Fifth Day of October, 2010

David J. Kappos
*Director of the United States Patent and Trademark Office*